(12) United States Patent
Wallin et al.

(10) Patent No.: US 6,374,825 B1
(45) Date of Patent: *Apr. 23, 2002

(54) DISPENSER UNIT FOR NON-GASEOUS FLOWABLE MATERIAL

(75) Inventors: Sten Wallin, Hägersten; Tom Pessala, Bromma; Pär Emtell, Vällingby, all of (SE)

(73) Assignee: Siemens-Elema AB, Solna (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/391,515

(22) Filed: Sep. 8, 1999

(30) Foreign Application Priority Data

Sep. 9, 1998 (SE) .............................. 9803048

(51) Int. Cl.[7] ............................................. A61M 15/00
(52) U.S. Cl. ............................ 128/203.14; 128/203.12
(58) Field of Search ....................... 128/203.12, 203.14, 128/203.19; 73/299

(56) References Cited

U.S. PATENT DOCUMENTS

| | | | | |
|---|---|---|---|---|
| 3,114,381 A | * | 12/1963 | Klose et al. ................. | 73/299 |
| 3,528,418 A | * | 9/1970 | Grosholz et al. ...... | 128/203.14 |
| 3,886,795 A | * | 6/1975 | Thompson .................... | 73/299 |
| 4,091,669 A | * | 5/1978 | Fehr et al. .................... | 73/299 |
| 4,527,600 A | | 7/1985 | Fisher et al. ................... | 141/4 |
| 4,567,761 A | * | 4/1986 | Fajeau .......................... | 73/299 |
| 4,611,590 A | * | 9/1986 | Ryschka et al. ........ | 128/203.14 |
| 4,630,478 A | * | 12/1986 | Johnson ....................... | 73/299 |
| 4,669,309 A | * | 6/1987 | Cornelius .................... | 73/299 |
| 4,675,301 A | | 6/1987 | Charneski et al. .......... | 436/180 |
| 4,922,852 A | | 5/1990 | Price .......................... | 118/683 |
| 5,022,557 A | | 6/1991 | Turner .......................... | 222/54 |
| 5,146,783 A | | 9/1992 | Jansche et al. ............... | 73/301 |

* cited by examiner

Primary Examiner—Aaron J. Lewis
(74) Attorney, Agent, or Firm—Schiff Hardin & Waite

(57) ABSTRACT

A dispenser unit for a non-gaseous flowable material has a holder for the flowable material with an aperture therein through which the material can be transferred between into and out of the holder, and a flow meter for measuring flow of the material during transfer. The flow meter has a sensor, for example a differential pressure meter which determines a pressure difference between two locations which are vertically spaced from each other within the holder, one above and one below the surface of the material, at a number of times during the transfer. The meter emits a signal indicative of the flow from a calculation of the rate of change of the determined pressure difference.

6 Claims, 2 Drawing Sheets

DISPENSER UNIT FOR NON-GASEOUS FLOWABLE MATERIAL

BACKGROUND OF THE INVENTION

1. Field of the Invention

The present invention relates to a dispenser unit for a non-gaseous flowable material, and in particular to a dispenser unit suitable for dispensing metered quantities of a material by measuring its flow.

2. Description of the Prior Art

Dispenser units which meter the amount of material dispensed by measuring the flow of the material from the unit are well known. A common method of measuring the flow is to measure the pressure difference developed across a flow restriction, such as an outlet of the dispenser, as material flows therethrough.

One known dispenser unit which operates according to this method is described in U.S. Pat. No. 4,922,832, and has a holder for pressurized fluid connected to a dispensing nozzle. A pressure transducer is provided to sense the fluid flow by measuring the pressure drop across the nozzle as the fluid flows. A valve is also provided which is controllable in response to the sensed flow to deliver a metered amount of the fluid through the nozzle. In order to measure very small flows, for example in the range of 0.005–20 ml/min, or fluctuations therein, the pressure transducer must be made extremely sensitive which is expensive and difficult to do. Moreover, the pressure transducer must be made very stable since drift in the baseline output with time can lead to inaccurate flow readings. Frequent calibration of the pressure transducer is often required to alleviate this problem, which is time consuming.

SUMMARY OF THE INVENTION

It is an object of the present invention is to provide a dispensing unit in which the problems associated with performing the pressure measurements to provide the flow information in known dispenser units are alleviated.

The above object is achieved in accordance with the principles of the present invention in a dispenser unit for non-gaseous flowable material having a holder for the flowable material with an aperture therein, through which the material is transferred (in either direction) between an interior of the holder and an exterior of the holder, a flow meter for measuring flow of the material during transfer through the aperture, the flow meter having a sensor which determines a pressure difference between two locations within the holder which are vertically spaced from each other, one above and one below the surface of the material in the holder, at a number of different times during the transfer, the sensor emitting an output signal indicative of the flow from a calculation of the rate of change of the determined pressure difference.

By using the rate of change of pressure difference between above and below the material in the holder, only sequential pressure measurements, taken over relatively short time periods, are needed. This reduces the effect that any pressure sensor baseline drift may have on the determination of the material flow. Moreover, the sensor need only have a linear response over small pressure ranges.

Additionally, sine the flow determination depends on the pressure developed by a material above a sensor, the dimensions of the holder can be readily adapted so that small changes in the amount of material in the holder produce large pressure changes at the sensor at the base of the holder (i.e. by making the holder relatively long and thin).

Preferably, the holder is sized to provide a material-free space above the material within it when full, and the through-flow aperture, through which the material is transferred between the internal and the external of the holder, is provided in the base. By having the sensor measuring the pressure difference between the material-free space and a location proximate the aperture, the flow of substantially all of the material is metered.

Simply, the pressure sensor may be a differential pressure meter so that an output indicative of the pressure difference between the measurement locations within the holder is obtained quickly and directly. Alternatively, the pressure sensor may have two individual units placed to measure the pressure one above and one below the material in the holder. In this latter case, the meter would require adaptation to determine the difference between the two sensed pressures.

Most usefully the dispenser unit may be employed as part of a liquid anesthetic delivery system where it is typically used to dispense metered quantities of liquid having small flows.

According to a second aspect of the invention, there is provided an anaesthetic delivery system including a dispenser unit for non-gaseous anaesthetic material having an aperture connectable to supply of a carrier gas for delivering into a breathing gas a metered quantity of anaesthetic material, wherein the dispenser unit is a unit as described above wherein the meter of that unit is adapted to provide an output signal indicative of the flow of anaesthetic material from the holder. This output signal can be usefully employed in the control of a valve which is disposed to regulate the flow of the anaesthetic material into the carrier gas and which is operably connected to the meter to automatically regulate the flow in dependence of the output therefrom.

DESCRIPTION OF THE PREFERRED EMBODIMENTS

Figure 1:
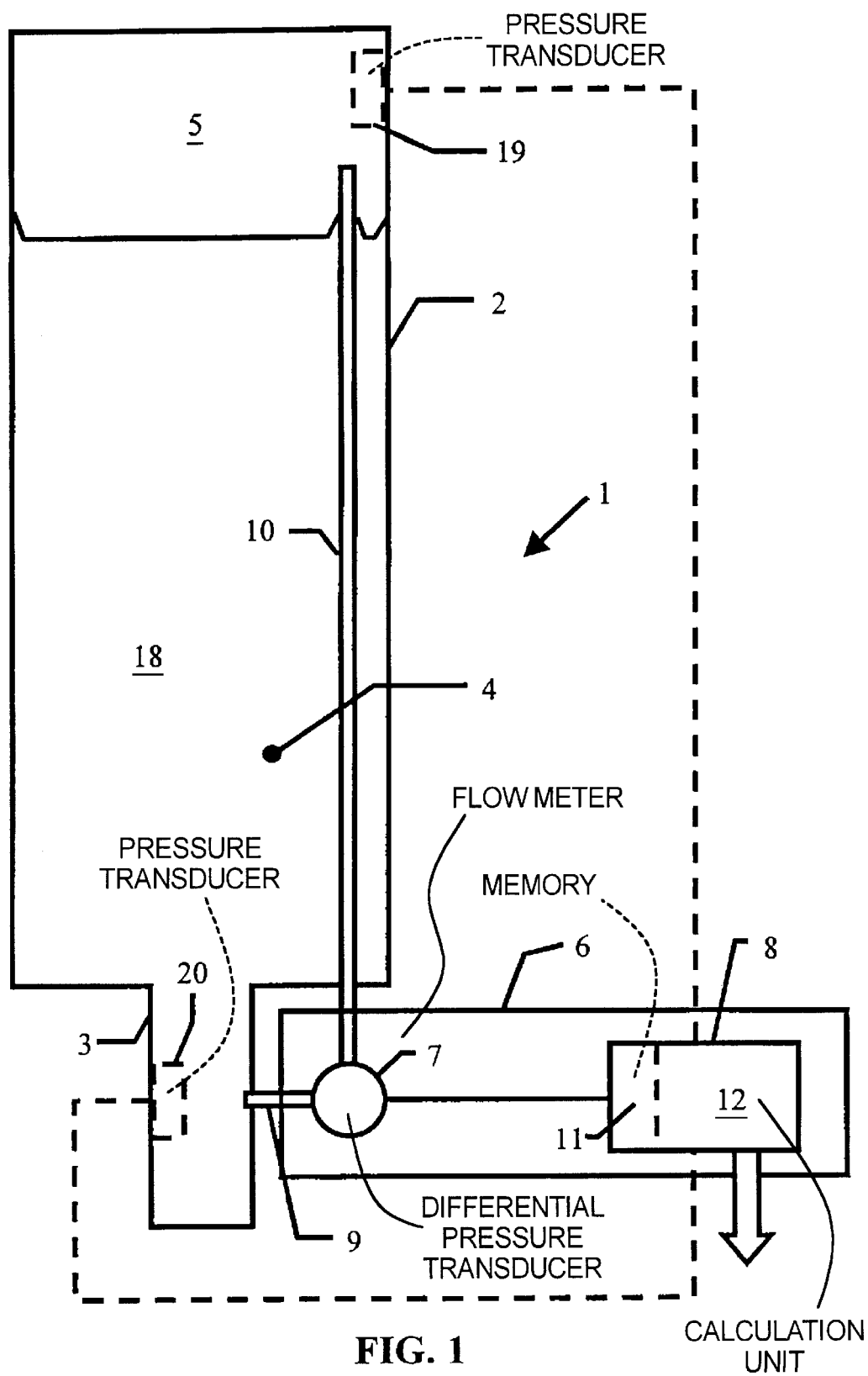
FIG. 1 is a schematic illustration of a dispensing unit according to the invention.

In FIG. 1, a dispenser unit 1, having a holder 2 having an outlet 3, is shown in its operating position. In this position the outlet 3 is located in the base of a material holding portion 18 of the holder 2, at the bottom of an amount of anesthetic liquid 4 which is to be dispensed from the holder 2. The maximum amount of liquid 4 which may be contained in the holder 2 is such that a section 5 of the holder 2 will, in its operating position, constitute a liquid-free space above the upper surface of the liquid 4.

The dispenser unit 1 also has a flow meter 6 which includes a differential pressure transducer 7 and a calculation unit 8 (which may be a dedicated microprocessor programmed using techniques common in the art). A first input of the transducer 7 is in pressure communication with the inside of the holder 2 proximate the outlet 3 via a capillary 99. A second capillary 10 extends through the region of the holder 2 occupied by the liquid 4 and terminates with an open end in the section 5 of the holder 2 which is a liquid-free space. The opposite end of the capillary 10 connects to a second input of the differential pressure transducer 7 to provide pressure communication between the liquid free space of the section 5 and the transducer 7. So configured, the pressure transducer 7 is adapted to measure the pressure difference ΔP between locations above and below the surface of the liquid 4 and outputs an electrical signal proportional to the measured difference to the calculations unit 8.

Alternatively, the differential pressure transducer 7 may be replaced by two pressure sensors 19, 20 respectively placed above and below the material 4 as shown by the broken lines in FIG. 1. The outputs from these sensors 19, 20 may then be fed to the calculation unit 8 which, in this alternative, determines the pressure difference between above and below the upper surface of the material 4 from the measurements from two sensors 19, 20.

Assuming that the holder 2 has a cross-sectional area A and contains a fluid of density ρ it cam be readily shown that the flow φ will be given by the equation:

$$\phi = (A/(\rho \times g)) \times (\Delta P1 - \Delta P2)/\Delta t) \qquad (1)$$

wherein g is the acceleration due to gravity;

ΔP1 is the measured pressure difference at a time t1;

ΔP2 is the measured pressure difference at a later time t2; and

Δt is the time difference t2−t1.

In this present embodiment the differential pressure transducer 7 may be operated to continuously measure the pressure difference ΔP and to provide the output signal. In this case, the calculation unit 8 may include a memory 11 which operates to periodically receive and store the output signal from the transducer 7. The processor unit 12, within the calculations unit 8, is configured to access the memory means 11 to retrieve stored pressure difference values ΔP and to then calculate their rate of change, and hence the flow φ using equation (1) above, from a knowledge of the time interval Δt between the storing of the two values in the memory 11. An electrical signal, indicative of the thus calculated flow φ, may then be output from the flow meter 6 for use external of the dispenser unit 1, for example, to drive a display and provide a visual indication of the calculated flow φ. or to provide control information to other equipment.

It will be appreciated by those skilled in the art that while in the foregoing embodiment the meter 6 is used to measure flow out of the holder 2, modifications encompassed by the present invention can be made which enable the meter to measure flow into the holder 2.

Figure 2:
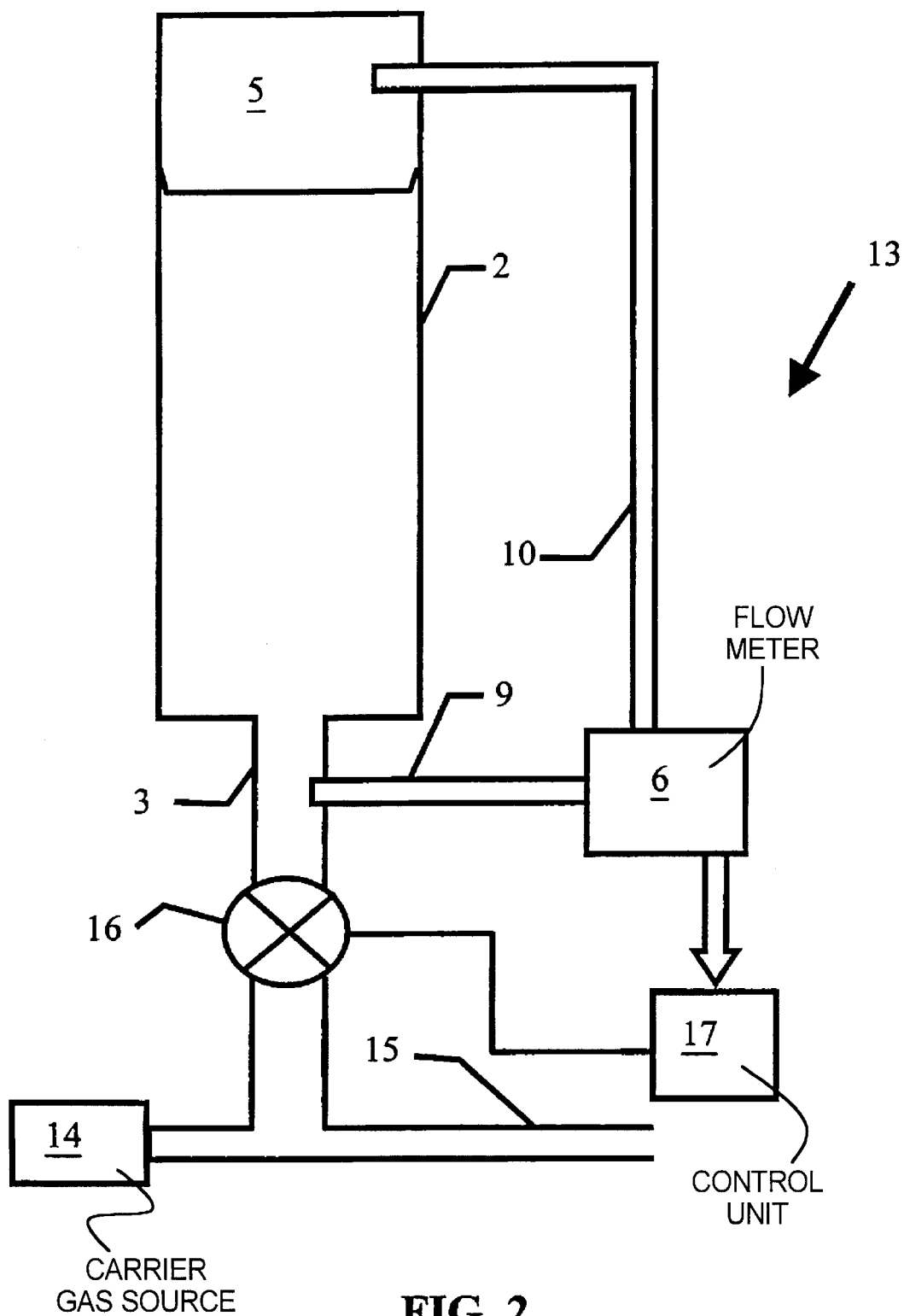
FIG. 2 is a schematic illustration of part of a anesthetic delivery system according to the invention.

A system incorporating the dispenser unit of FIG. 1 is shown in FIG. 2 and constitutes an anesthetic delivery system 13. A source of carrier gas 14 is connected to a delivery conduit 15 which itself is connectable with a breathing gas conduit of a patient ventilator system (not shown). A liquid anaesthetic holder 2 is connected in liquid communication with gas in the delivery conduit 15 via a valve 16 which operates to automatically vary the flow of anesthetic from the holder 2 in response to control signals from a control unit 17. The flow meter 6 determines the flow from the holder 2 and outputs a signal representative of the determined value to the control unit 17, which then processes the signal to operate the valve 16 dependent on the determined flow value in order to achieve a desired concentration of anaesthetic in the carrier gas.

Although other modifications and changes may be suggested by those skilled in the art, it is the intention of the inventors to embody within the patent warranted hereon all changes and modifications as reasonably and properly come within the scope of their contribution to the art.

We claim as our invention:

1. A dispenser unit for a non-gaseous flowable material, comprising:

a holder for non-gaseous flowable material having an aperture through which said material flows in a transfer of said material between an interior of the holder and an exterior of the holder, said material in said holder having a surface; and a flow meter comprising a sensor which determines a pressure difference, at a plurality of times during said transfer, between two locations within said holder vertically spaced from each other, one of said locations being above said surface and one of said locations being below said surface, said sensor emitting a sensor output signal representing said pressure difference, and a calculation unit supplied with said sensor output signal which calculates a rate of change of said pressure difference and emits a signal representing said flow of said material through said aperture from said calculation of said rate of change of said pressure difference.

2. A dispenser unit as claimed in claim 1 wherein said holder has a material-free portion above said surface and wherein said material in said holder has a bottom, with said sensor being proximate said bottom of said material in said holder, and wherein said sensor determines said pressure difference between a location proximate said aperture and a location within said material-free portion.

3. A dispenser unit as claimed in claim 1 wherein said sensor comprises a differential pressure transducer in pressure communication with said two locations.

4. A dispenser unit as claimed in claim 1 wherein said sensor comprises a first pressure element and a second pressure element respectively disposed to measure pressure at said two locations, each of said first and second pressure sensor elements emitting an output signal to said calculation unit.

5. An anaesthetic delivery system comprising:

a supply of carrier gas for delivering a metered quantity of non-gaseous, flowable anaesthetic material into a breathing gas; and a dispenser unit for supplying said metered quantity of non-gaseous anaesthetic material to said supply of carrier gas, said dispenser unit comprising a holder for said non-gaseous flowable anaesthetic material having an aperture through which said material flows in a transfer of said material between an interior of the holder and an exterior of the holder, said material in said holder having a surface, a flow meter comprising a sensor which determines a pressure difference, at a plurality of times during said transfer, between two locations within said holder vertically spaced from each other, one of said locations being above said surface and one of said locations being below said surface, said sensor emitting a sensor output signal representing said pressure difference, and a calculation unit supplied with said sensor output signal which calculates and emits a signal representing said flow of said material through said aperture from a calculation of a rate of change of said pressure difference.

6. An anaesthetic delivery system as claimed in claim 5 further comprising an automatic flow control valve disposed to regulate the flow of anaesthetic material into the carrier gas and connected to said flow meter to regulate said flow dependent on said output signal from said flow meter.

* * * * *